United States Patent [19]

Holbrook et al.

[11] 3,998,227

[45] Dec. 21, 1976

[54] REGULATOR STRUCTURE AND SYSTEM

[75] Inventors: LeGrand K. Holbrook; Silas Charles Topham, both of Salt Lake City, Utah

[73] Assignee: Medical Development Corporation, Salt Lake City, Utah

[22] Filed: July 23, 1975

[21] Appl. No.: 598,374

Related U.S. Application Data

[63] Continuation-in-part of Ser. No. 505,784, Sept. 13, 1974, abandoned.

[52] U.S. Cl. .......................... 128/276; 137/556.6; 251/207; 251/209; 137/625.41
[51] Int. Cl.² ................. A61M 1/00; F16K 11/02
[58] Field of Search ............. 137/553, 556, 556.3, 137/556.6, 625.41; 251/207, 209; 128/276, 277, 278; 141/8, 59, 65, 32, 33

[56] References Cited
UNITED STATES PATENTS

| | | | |
|---|---|---|---|
| 3,612,100 | 10/1971 | Kapeker | 137/556.6 |
| 3,853,138 | 12/1974 | Amren | 137/205 |
| 3,855,997 | 12/1974 | Sauer | 128/276 |

Primary Examiner—William R. Cline

[57] ABSTRACT

A regulator for evacuation systems including hospital aspiration systems, such regulator being inexpensively manufactured and assembled and providing a number of unique features. The subject regulator is designed to be essentially independent of altitude of operation or humidity conditions, may be made discretely or continuously variable, and also is provided with features reducing, if not eliminating, any noise of air drawn into the system for regulation purposes. An important feature of the invention is the provision of one or more metering apertures of reduced cross section such that possible error of observable knob setting is reduced to an absolute minumum, thus eliminating the necessity of mechanical-adjustment calibration. Settings are essentially accurate for all altitudes, humidity conditions, and particular pumping parameters of existing vacuum systems. The particular metering apertures, above referenced, are serially related to a unique, slotted airway metering pattern designed to give wide versatility through extended permissible settings. Full-vacuum, and shut-off structural features are also provided.

30 Claims, 34 Drawing Figures

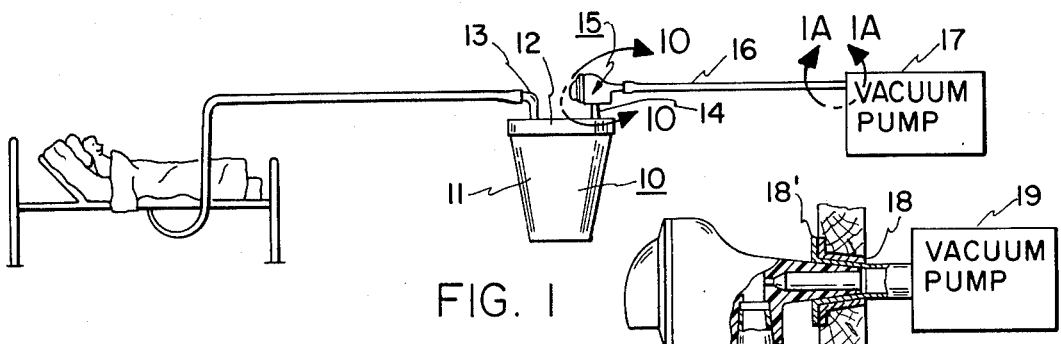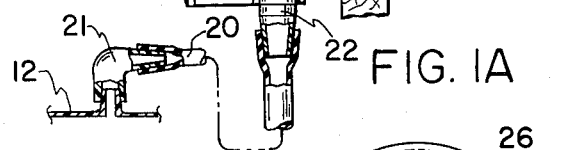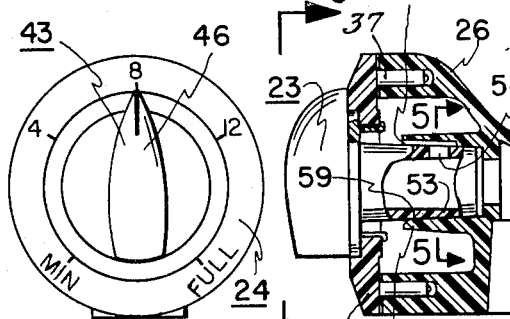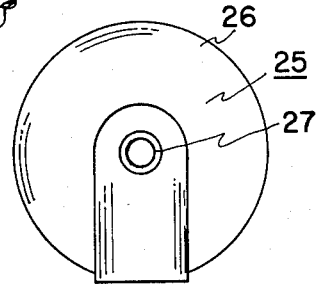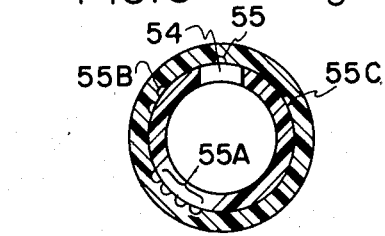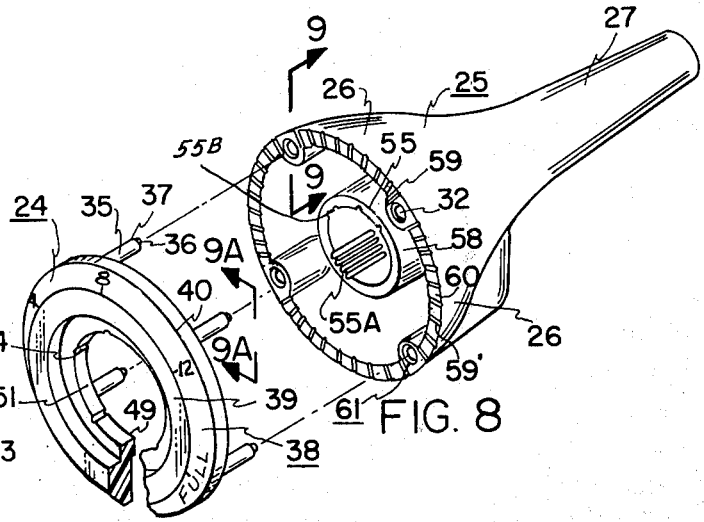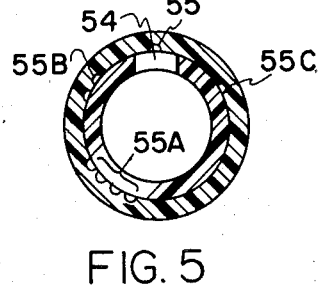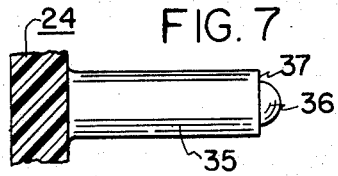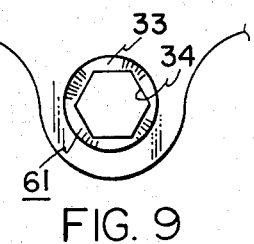

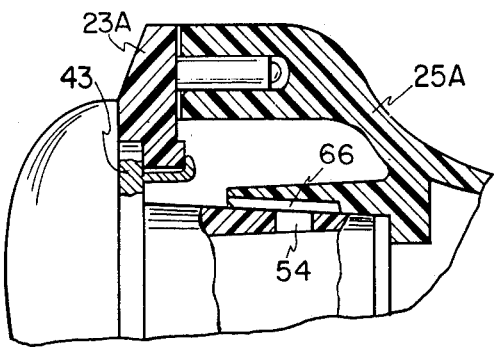
FIG. 12A
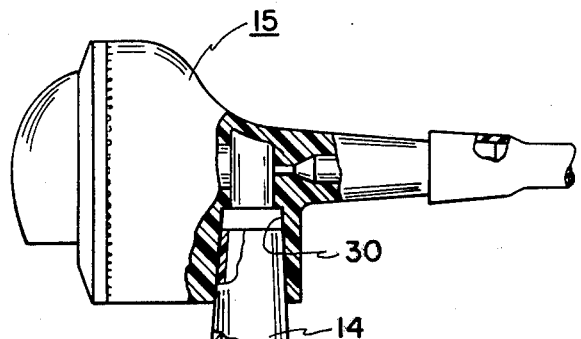
FIG. 10
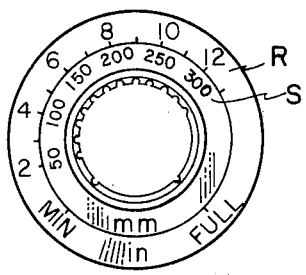
FIG. 13
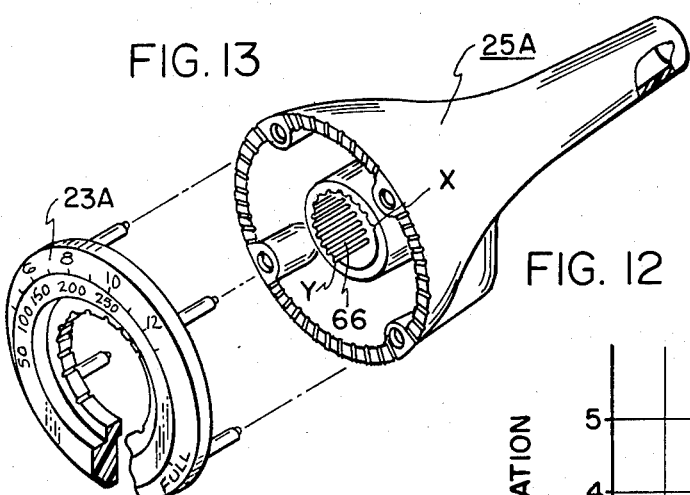
FIG. 12
FIG. 11
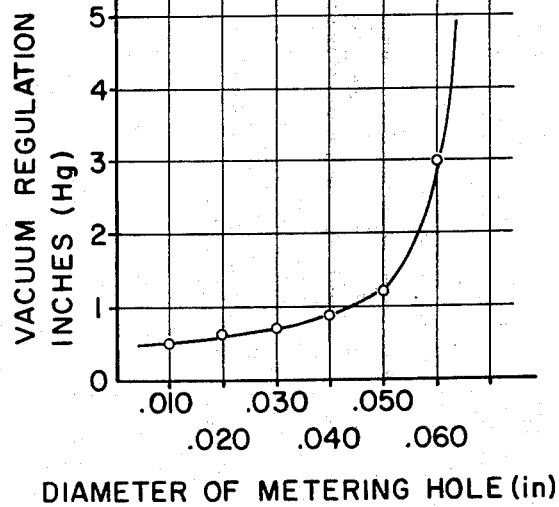
FIG. 14

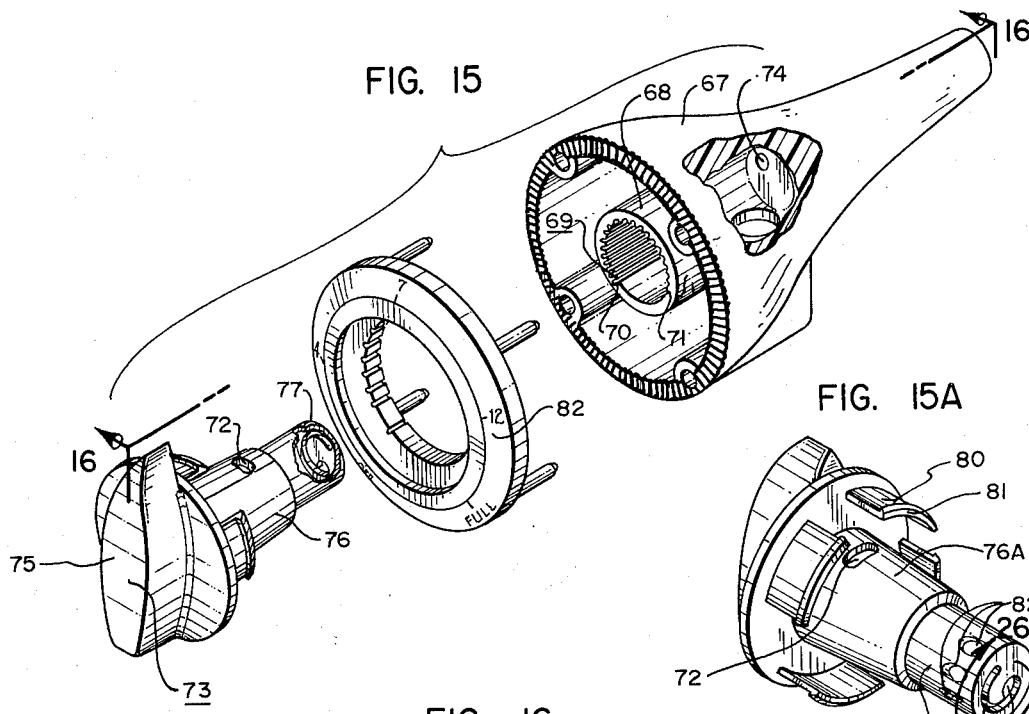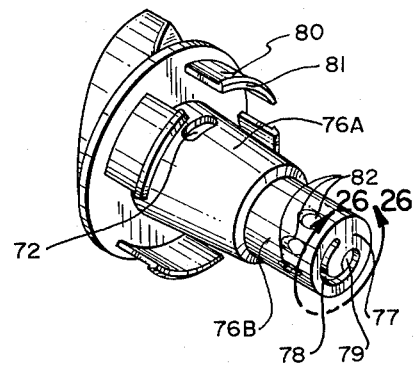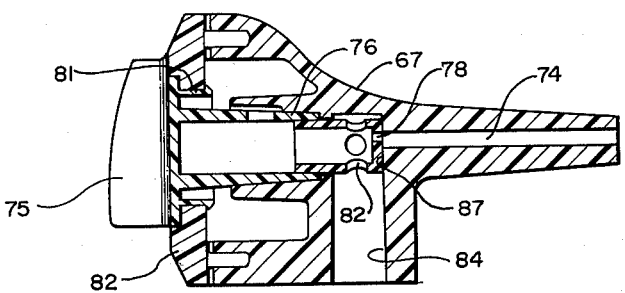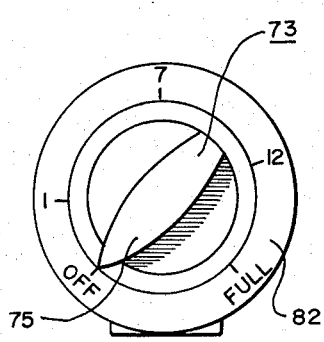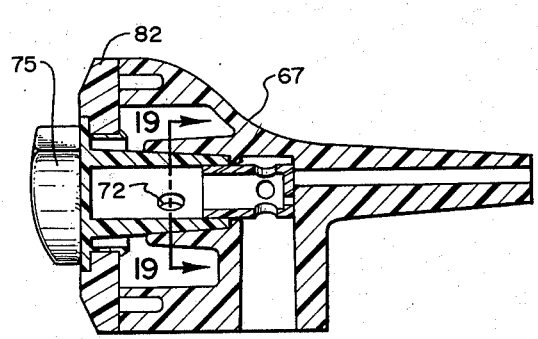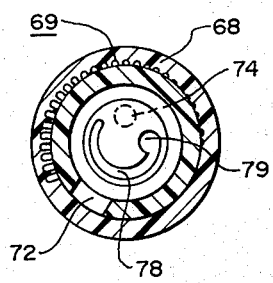

REGULATOR STRUCTURE AND SYSTEM

This is a continuation in-part of pending application by the same inventors entitled VACUUM-SYSTEM REGULATOR STRUCTURE, Ser. No. 505,784, filed Sept. 13, 1974 and now abandoned.

The present invention relates to regulators useful in vacuum systems, aspiration systems, and the like, and more particularly, to a new and improved regulator which is inexpensively manufactured but which performs in a highly satisfactory manner through a wide variety of potential operating conditions.

Past regulators, in addition to being quite expensive to fabricate and assemble, must be calibrated and often are quite cumbersome to install and operate. A number of different regulators, in fact, must be re-calibrated each time for different altitude usages. Furthermore, humidity factors and volumetric pumping characteristics of various vacuum systems play an important part in requiring continuous attention as to calibration of the regulators so that readings thereof will accurately reflect the absolute vacuum condition within the regulated system. Many other regulators incorporate various types of valves, springs, pivots, jewels and diaphragms, all of these being subject to malfunction.

In the present invention the regulator may be attached directly to a liquid collection bottle, tied into a vacuum line, or simply coupled to the vacuum side of a vacuum pump or directly to the wall connection of a vacuum system. This is believed the first instance of a simple regulator having a manual, permanently-calibrated pointer-control which with its dial reflects true vacuum conditions without further adjustment.

Other features include, in one embodiment, a small metering aperture that ensures that the regulator will not need re-calibration for various altitudes or other operational parameters. The full and exact disclosure herein sets forth processional requirements of such metering aperture wherein the regulator will not have to be calibrated for differences in altitudes of operation, differing humidities of ambient air, and parameters of vacuum pumping system. Also, in other embodiments thereof, a series of selectively-registerable, metering-aperture constrictions are provided; alternatively, a curved, end slot or channel is configured, with "open" and "closed", suitable configured structural regions, for providing the necessary passageway constriction needed.

The subject regulator provides for a drawing-in of air essentially completely circumferentially about the regulator, this using a plurality of air inlet slots such that the generation of objectional noise by such ingress air is essentially eliminated. An interior, discretely or continuously variable air metering system provides for a variable passage of air from the exterior and through the metering apparatus, so that variable vacuum conditions may be achieved by use of such regulator.

Accordingly, a principal object of the present invention is to provide a new and improved regulator for vacuum systems.

A further object is to provide an improved regulator, which is not subject to error between setting and actual condition, which otherwise might be produced through physical shock.

An additional object is to provide a new and improved regulator for fluid aspiration systems, as for hospital and other usage, that can be mounted directly to the aspiration bottle.

An additional object is to provide an inexpensively produced regulator for use in various types of vacuum systems.

An additional object is to provide a regulator incorporating a metering aperture principle of reduced dimension, whereby the regulator will not require periodic maintenance so far as periodic recalibration is concerned, differences in altitudes of operation, usual vacuum pump parameters, humidity conditions, and so forth.

An additional object is to provide a new and improved regulator having a minimum or no noise-generating capacity.

An additional object is to provide in a regulator a slot registration system wherein the volume of outside air admitted into the regulator can be regulated as to passage thereof into the vacuum system proper.

A further object is to provide a regulator wherein the control and/or housing thereof are designed to admit of metered, full-vacuum and closed conditions, with ambient air-draw being preferably eliminated during the latter two conditions.

The features of the present invention may best be understood taken in connection with the accompanying drawings in which:

FIG. 1 is a diagrammatic view of a hospital patient accommodated by an aspiration system incorporating the regulator of the present invention at the aspirator bottle point.

FIG. 1A is similar to FIG. 1, as shown in fragmentary view, and illustrates merely that the regulator may be attached directly to the conventional valve fitting or socket in the wall of the hospital rather then to the aspiration bottle proper, being taken along line 1A—1A in FIG. 1.

FIG. 2 is an enlarged side elevation, partially broken away and sectioned, of the assembled regulator invention.

FIGS. 3 and 4 are end views of the regulator structure of FIG. 2 and are respectively taken along the lines 3—3 and 4—4.

FIG. 5 is an enlarged transverse section taken along the line 5—5 in FIG. 2.

FIGS. 6, 7, and 8 in the aggregate comprise an exploded view, and singlely, comprise respective views of the control member, bezel, and base housing, respectively, constituting the regulator.

FIG. 9 is an enlarged view taken along the line 9—9 in FIG. 8.

FIG. 9A is an enlarged, partially-sectioned view taken along the line 9A—9A in FIG. 7, illustrating the configuration of the guide-lock pins that cooperate with the side apertures of the housing.

FIG. 10 is an enlarged view, partially sectional, and taken along the accurate line 10—10 in FIG. 1, illustrating the manner of mounting of the regulator to the vacuum port of a container lid or cover.

FIGS. 11 and 12 are perspective views and, in the aggregate, constitute an exploded view, of a modified benzel and base housing wherein the same is constructed for continuous variation rather for incremental variation as in FIG. 2.

FIG. 12A is an enlarged, fragmentary partially-sectioned detail of the completed regulator of FIG. 12 wherein the control member is assembled therewith. Other than those aspects pointed out with reference to FIGS. 11 and 12, the composite structure of 12A remains essentially the same as that shown in FIG. 2.

FIG. 13 is an enlarged fragmentary view of the face of the modified bezel indicating that the same may display a regulator-set vacuum reading in both inches and millimeters of mercury.

FIG. 14 is a graph illustrating the regulation that can be achieved at and about the metering aperture dimensions given relative to the metering airway in the base housing as hereinafter described.

FIG. 15 is an exploded perspective view of an alternate form of the invention, and is similar to FIG. 6, 7, and 8.

FIG. 15A is a perspective of the control employed in FIG. 15.

FIG. 16 is a longitudinal vertical section of the structure of FIG. 15, when taken along the line 16—16.

FIG. 17 is similar to FIG. 3 but illustrates the "off" setting of the control in FIG. 15 when both the vacuum container and ambient regulator air are shut off from the pump.

FIG. 18 is similar to FIG. 16 but illustrates aperture and slot misalignment when the regulator is in the off condition.

FIG. 19 is an enlarged transverse vertical section taken along the line 19—19 in FIG. 18.

Figure 20:
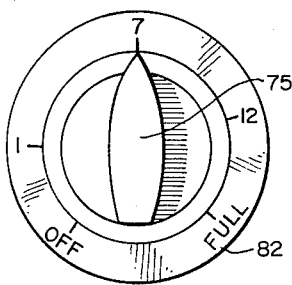
Figure 21:
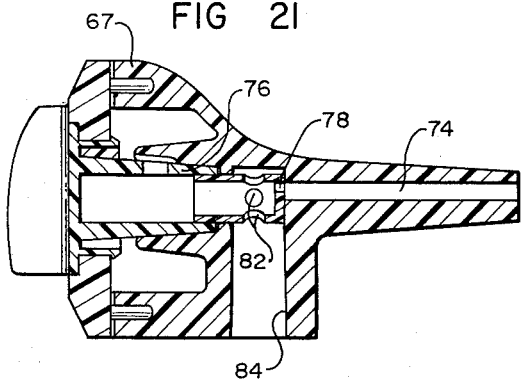
Figure 22:
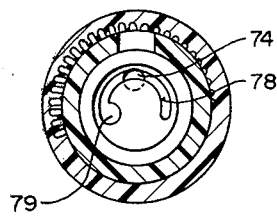

FIGS. 20–22, respectively, correspond to FIGS. 17–19 and illustrate where the control is now oriented for a selected, medium vacuum condition.

Figure 23:
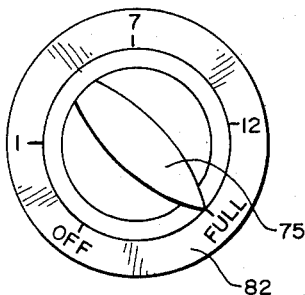
Figure 24:
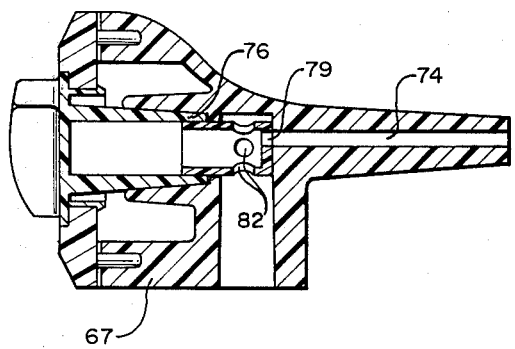
Figure 25:
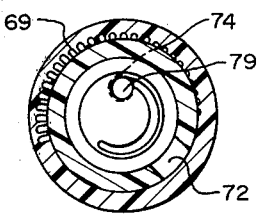

FIGS. 23–25 are respectively similar to FIG. 20–22, respectively, but now illustrate passageway and aperture positionment when the control is adjusted for full vacuum condition.

Figure 26:
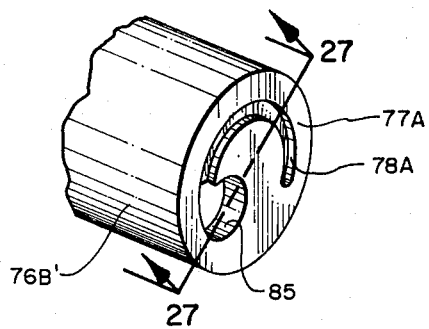

FIG. 26 is an enlarged, fragmentary, perspective view taken along arcuate line 26—26 in FIG. 15A.

Figure 27:
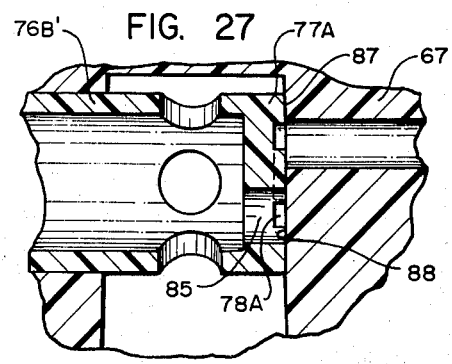

FIG. 27 is an enlarged, transverse section, taken along the line 27—27 in FIG. 26, illustrating recess registration with the air outlet of base housing of the regulator at a particular position of the control with respect to the base housing.

Figure 28:
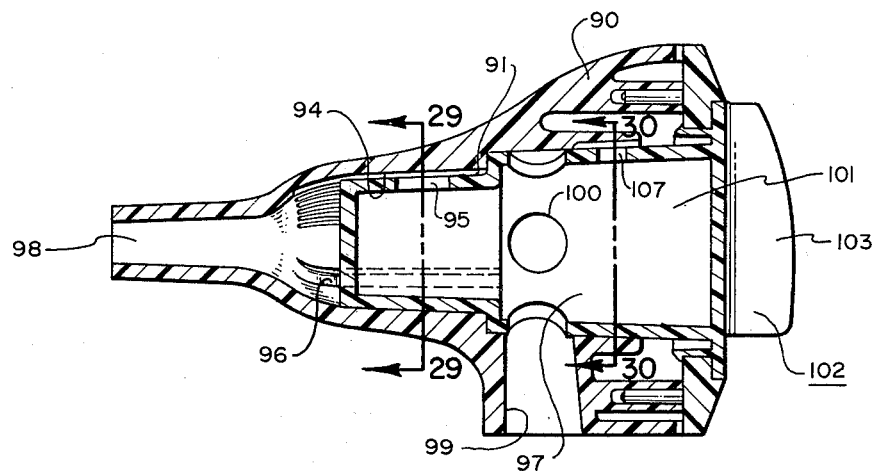

FIG. 28 is a longitudinal vertical section of another form of regulator, representing another embodiment of the invention, wherein the forward extension of the vessel cooperates wit the annular, interior slot or passageway pattern providing the essential metering function as herein described.

Figure 29:
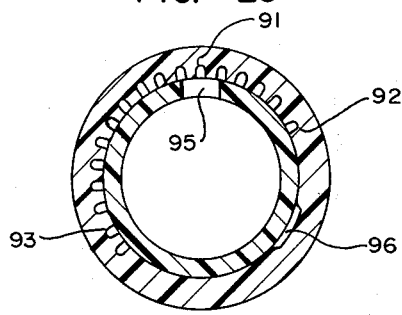

FIG. 29 is an enlarged transverse section taken along the line 29—29 in FIG. 28.

Figure 30:
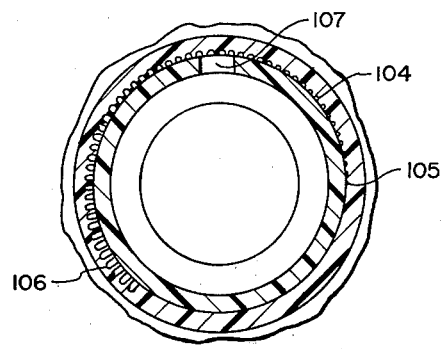

FIG. 30 is an enlarged transverse section taken along the line 30—30 in FIG. 28.

By way of introduction, it is to be observed throughout the detailed descriptions of various selected embodiments as hereinafter set forth, that the subject regulator and system are adaptable for simply a teed connection to a vacuum line, for direct mounting to a negative pressure supply port leading to an aspiration vessel, or for direct connection to such aspiration vessel. In the invention a mountable bezel is designed to admit ambient air in a peripheral manner into the base housing carrying the bezel. Intercooperable structures of the housing, and bezel control provide variable "leakage" into the interior of such housing. The "air outlet" of the housing is provided with a metering facility represented by an air passage having not greater than 0.002 square inches, so that regulation can be effective over a wide range of altitudes and under a wide range of conditions. Such air-passage restriction at the output of the regulator renders more effective the inlet air leakage past the bezel in controlling the negative pressure within an aspiration vessel.

In FIG. 1 an aspiration bottle 10 includes container 11 and cover 12 sealingly secured thereover in a conventional manner. Cover 12 includes fluid inlet port 13 and also vacuum port 14. The regulator 15 of the present invention is secured to the latter port and finds connection with conduit 16. Conduit 16 leads to conventional vacuum pump 17 shown in block diagram form.

FIG. 1A illustrates that in lieu of the direct connection of the regulator 15 to the vacuum port of the cover 12, the regulator may be connected directly to an adaptor 18', if needed, and when used, fitted into wall receptacle 18 leading to a stationary vacuum supply 19. In such event, the tube 20 will be connected from the L-configured vacuum port 21 of the aspiration bottle 10 to an adaptor fitting 22 inserted into regulator 15. In any event, it is seen that the regulator in its construction is suitable for connection directly to the aspiration bottle as well as any wall-mounted vacuum supply as in FIG. 1A.

In any event, FIG. 2 illustrates that the regulator 15 is comprised essentially of three parts, namely, a control member 23, a bezel 24, and a base housing 25. Base housing 25 is provided with a principal portion 26 and a connection extension 27 integral therewith. Connection extension 27 includes an air passageway 28 which is contiguous with and communicates with a metering airway 29. The cross-sectional area of metering airway 29 is restricted and such restriction is most important. Where of cylindrical nature, the passageway or aperture 29 must be restricted in diameter to 0.050 inches or less, and preferably 0.040 inches. Other than circular cross sections, the metering airway 29 should have a cross-sectional area no greater than 0.002 square inches (i.e. $3.14 \times (.050 \times .5)^2$); where such a constriction is preserved at 29, then the regulation desired, i.e. a variation of approximately one inch mercury, regardless of setting and altitude of operation, is preserved. This is most important. Thus, regardless of the altitude of operation, a given regulator setting will maintain a constant negative pressure in the vacuum system, leading to aspiration bottle 10, regardless of changes in either altitude or humidity. By experimentation, it has been shown that the margin of error does not exceed about 1-¼ inches of mercury differential over the entire range of operation of the regulator from 0 to 29 inches of mercury (i.e. full vacuum). Additionally, accuracy in calibration is maintained through a wide range of vacuum pumping conditions, both volumetric pumping and vacuum pressure-level conditions.

Accordingly, and regardless of the size or characteristic of the usual vacuum pump means, and, additionally, regardless of the humidity and altitude of operation, the provision of this metering passageway will ensure great accuracy of the regulator to within about 1-¼ inches of mercury for any setting taken on the regulator. Thus, the above-described operation relative to the metering airway is very important.

In returning to make consideration of the details of the remaining structure of base housing 25, it is seen that the same includes an interior mounting seat 30 that is contiguous with central aperture chamber 31. Principal portion 26 includes a series of alignment guide-lock apertures 61 which, in one form of the invention, may be provided with a chamfered lip 33 contiguous with hexagonal sides 34. The guide-lock pins 35 are pressed into the guide apertures 61 such that the round areas are frictionally engaged by the hexagonal sides 34 of the guidelock receiving apertures. These guide-lock pins may be molded integrally with the remainder of the bezel construction at 24 and, for convenience of molding, may include rounded ends 36 surrounded by abutment shoulders 37. These latter features simply serve to facilitate the molding operation.

Bezel 24 includes an annular ring 38 provided with straight and chamfered annular surfaces 39 and 40. The latter may be provided with indexing numbers and markings to cooperate with the index line 41 and tip 42 of the knob portion of control member 23.

Bezel 24 includes a series of detents 44 for receiving the rotatable, raised detent protuberance 45 of control member 23.

In addition to including knob portion 46, the control member 23 includes a central disk-like portion 47 provided with flange-like detent fingers 48, one having the raised detent protuberance 45. The fingers 48 serve as retainer fingers for comping in retentive engagement with side 49. The parts may be made of a suitable plastic such as a high-density ABS plastic, and the fingers 48 are tapered at 50 so that these may be easily pushed through the central circular opening 51, thereby allowing the fingers 48 to snap in place on the opposite side of the bezel.

Control member 23 includes a central, hollow, tapered fusto-conical boss or tapered cylinder portion 53 which is provided with a wall slot or aperture 54 as seen in FIGS. 2 and 6–8. The aperture 54 is selectively positioned in engagement with one or more interior longitudinal wall slots 55. The group of four wall slots at 55A in FIG. 5 is shown also in FIG. 8. A single wall slot 55 is positioned in registry with aperture 54 in FIG. 5. It will be seen relative to FIGS. 2 and 6 that the tapered boss 53 fits into an airway boss portion 58. The latter itself is provided with interior tapered surface 59 having slot patterns at 55, 55A–55C.

Finally, the base housing 25 is shown to include air passageway 59 and a series of notches or air escape slots 59' on annular, edge surface 60 of principal portion 26 of such member. The purpose for this is to admit air ingress over a wide area, namely, essentially 360° about base housing 25, and at the same time exclude the passage of lint or other foreign matter from the internal regulator structure, so that, also, there will be no noise or whistling effect as might be produced through the drawing in of an equivalent volume of air through a lesser number of restrictions.

In assembly, see FIGS. 2 and 6–8, the control member 23 including knob portion 46 is thrust mounting engagement with bezel 24 by the chamfered retainer fingers 48 being thrust through the central opening 51 of the bezel until the fingers engage the opposite side surface of such bezel. At this point the protuberance 45, for detent purposes, is available for selective engagement with a selected notch 44.

Th combination of the control member 23 and bezel 24 is next mounted to base housing 25 by the guidelock pins 35 being thrust into the lock-pin apertures 61. The flat hexagonal side 34 will frictionally engage the sides of the guide-lock pins 35 so that these will be frictionally retained in an appropriate manner. The hollow boss portion 58 is shown to overlap cylindrical portion 53 in the embodiment shown, though the reverse may be the case. In assembly, it is noted that the succession of slot passageways as at 55A in FIG. 8 will be in selective registry with aperture 54 of the control member 23.

In opertion, the mounting portion 30 in FIG. 2 receives the upstanding port 14 of the lid or cover 12 of aspiration bottle 1 in FIG. 1. See also FIG. 10. The invention includes the concept of providing a variety of a slot or passageway pattern relative to the airways at 55, 55A, and so forth. In one embodiment of the invention, see FIG. 5, the airways are of uniform depth but of different groupings, i.e. one, two, or four, for example, either of similar of varying depth. In general, the aperture or slot at 54 will be of greater transverse dimension than the width of any particular passageway in FIG. 5, or perhaps group of passageways, so that there will be either a small or large width slot at 55 and 55C in FIG. 5 in registry with wall aperture 54, or, indeed, the wall aperture 54 may encompass the entire series of slots at position 55A.

FIG. 12 represents a similar embodiment of the invention, but indicates a succession of air passageways, airways, or slots at 66 that may be of progressively increasing depth or width, from point X to point Y, for example. Thus, even though the registering wall aperture 54 in FIG. 12A registers with the same number of slots in FIG. 12, the composite air passageway through the overlapped airways and wall slot 54 will provide for a progressively increasing admittance of outside air at the lower indexed regions of the bezel in FIG. 11 as the control member 23, also used in conjunction with the combination in FIG. 12, is rotationally displaced to the lower end. At essentially full-vacuum conditions in FIG. 11, by way of example, there will be very little, if any, air drawn in through wall aperture 54; thus, there will be very little or essentially no air drawn into the vacuum system, so that essentially full-vacuum conditions are maintained.

FIG. 13 illustrates in lieu of a single series of indexing numbers indicating inches of mercury, that there may be plural indicia at R and S indicating both inches and centimeters of mercury (Hg.) relative to existing vacuum or negative pressure.

The structure in FIG. 12A is similar to that in FIG. 2, but this time illustrating the cooperation of base housing 25A, corresponding to base housing 25 in FIG. 8, with the new bezel 23A corresponding to bezel 24 in FIG. 8.

The graph in FIG. 14 simply graphs vacuum regulation, i.e. maximum deviation from regulator setting of all actual negative pressures exhibited by the system over a wide range of altitudes (sea level to 4,600+ feet), humidity, and vacuum pumping conditions, and the metering effect obtained when the hole size at 29 in FIG. 2 is restricted in the manner indicated. Clearly, as the graph illustrates, optimum regulation results are achieved for hole diameter of 0.040 inches, with the "knee" of the curve, indicating maximum hole size at 29 in FIG. 2, or being 0.050 inches in diameter.

What is provided, therefore, is a new and improved regulator for vacuum systems, particularly in hospital aspiration systems, wherein the vacuum fluid is regulated through the ingress of outside air through the regulator into the vacuum system. A number of features are present including ease of assembly and of manufacturing cost. Note the drawing of air through the notches or passageways as at 59 ensures an omnidirectional intake of air completely about the peripheral of the edge 60 proximate the principal portion of the base housing 25. Thus, there will be a minimum of volume drawn in as to any particular slot or airway 59' so that no noise factor will be present in the "sucking in" of outside air.

Of course, even though such air is present as through the slot pattern proximate edge 60 in FIG. 8, essentially no air will proceed through the regulator until the knob portion 46 of integral control member 43 is rotated such that registration aperture 54 engages one of the slot patterns as at 55, 55A, 55B, and so forth.

The user will select the particular interior vacuum condition desired i.e. one to twelve inches of mercury or even full vacuum, and can be confident that regardless of the humidity of the outside air, the location as to altitude of the device, and even the volumetric characteristics and vacuum pressure level of the vacuum system used as per vacuum pump 19, that the index marking on bezel 24 will indicate essentially exactly, the exact vacuum condition maintained in the vacuum line leading to aspiration bottle 19.

The embodiment shown in FIGS. 6–8 illustrates a regulator with discrete settings from a designated minimum through 4, 8, 12 inches of mercury on up. The unit in FIGS. 11, 12, and 12A, in contrast, illustrates a continuously variable regulator wherein a multitude of settings may be achieved. Again, as to the latter embodiment, this is had by a continuous series of slots 66 of progressively increasing depth or width but of perhaps uniform spacing.

As to air passageway 29 the same way, of course, comprise a series of small passageways having a combined transverse open area not greater than 0.002 square inches.

In FIG. 15 base housing 67 is similar to housing 25 in FIG. 8, but this time hollow base portion 68 includes a series of slotted air passageway 69 which proceed from a point at which time the slots are deepest at 70 to where the slots are shallowest at 71. These cooperate, of course, with aperture 72 of control or control member 73. Hollow base portion 68 again is similar to the base portion in FIG. 8; this time, however, air outlet 74 is full-sized, i.e. it has no restriction as at 29 in FIG. 2. Instead, control member 73, in addition to having knob portion 75, includes a forwardly tapered cylinder 76 having an end 77. See FIGS. 15 and 15A. End 77 included an arcuate slot 78 that terminates in an enlarged "full" vacuum aperture 79. The cylinder 76 may be comprised of a central hollow boss 76A and also an elongate, cup-like extension 76B cemented thereto and provided with end 77. Fingers 80 are provided and include radially extending tapered flanges 81 which provide for a thrusting insertion of control member 73 through bezel 82 to lock together in the manner shown in FIG. 16, and to secure end 77 against seat 87.

FIG. 16 illustrates the manner by which the cylindrical portion 76, whether of a one-piece or a two-piece construction as shown in FIGS. 15 and 15A, respectively, seats within the housing 67. A series of apertures at 82 will be provided so as to afford communication between the inner portion or of the cylindrical member 76 and the aspiration bottle connection port 84.

As to aperture 74, it is seen that in general this aperture will be in the same vertical plane but raised relative to the axis or cylindrical portion 76. The slot 78 may be disposed completely through end 77 in the manner shown in FIGS. 15A and 16. Alternatively, as seen in FIGS. 26 and 27, member 76B', corresponding to part 76B in FIG. 15A, may have its end at 77A, corresponding to end 77 in FIG. 15A, simply recessed at slots 78A rather than carry this "slot" completely through such end 77A. In this event, however, the recess 78A, comprising the metered or restricted air passageway, will communicate with the enlarged aperture 85 provided for full vacuum condition. See in this connection the aperture 85 in FIG. 27, and see also FIG. 26. Thus, it is noted, that since the end 77A in FIG. 27 abuts seat 87 of base housing 67, then the passageway constriction is formed by a channel, i.e. slot 78A with its cooperation with face 88 supplying the seat by for the extension cylinder 76B'.

FIG. 17, 18, and 19 are views of te structure wherein the knob is placed in the "off" position, i.e. where wall aperture 72 will be disposed completely out of registry with the air passageways 69 in FIG. 15. At this juncture, however, the air outlet passageway 74 is likewise out of registry both with slot 78 and also its terminating, enlarged full vacuum aperture 79.

FIGS. 20–22 correspond to FIG. 17–19, excepting that in the case of FIGS. 20–22 a medium leakage flow condition is illustrated. This is seen wherein the knob 75 is turned appropriately to a medial position. In such event air outlet end 74 is only slightly in registry with slot 78 of cylindrical portion 76. Thus the slotted passageway at 78 merely rides over a "corner" or a very small sector of enlarged passageway 74. The combination of the slot and passageway, i.e. slot 78 and passageway 74, will be such that, at their intersection or juncture, a cross section of only .002 square inches will exist. Thus, the passageway 78, is just the same as traveling over a corner of aperture 74, will be sufficiently smaller in width dimension at the overall constriction, formed of airway 74 and the sector of the slot 78 in registry therewith, will measure only the .002 square inches or less.

FIGS. 23–26 illustrate a full vacuum or full flow condition wherein the enlarged aperture 79 is brought into full registry with air outlet 74. In such a condition there is a maximum registration of aspiration port 84 with air passageway or air outlet 74 so that a maximum air drawing affect will take place. Note also is to be made that at this point the wall aperture 72 will be completely out of registry with a series of air passageways 69 as seen in FIG. 16 and especially FIG. 25.

In FIGS. 28–30 base housing 90 is made slightly differently in the sense that, this time, the several passageways at 91, 92, 93 and so on will be mutually spaced and registerable with a wall slot 95 separately. Thus, these apertures 92, 93 serve as metering apertures and will have overall transverse cross sections at at lease one point of .002 square inches or less. There will be a recess at 96 in the interior of base housing 90, as shown, to provide for a full-flow condition from the interior of the cylindrical member 97 to air outlet 98. Aspiration container port 99 is provided and communicates with apertures 100 in the cylindrical part 101 of control member 102, the latter being provided with knob 103. FIG. 30 illustrates a series of air passageways 104, which commences with the shallow passageways at 105 and extending to the deepest passageways 106. These will be similar to those passageways at 55A in FIG. 8 or at 69 in FIG. 15, and at any event either one or more will register with wall aperture 107. In other aspects the regulator construction may remain essentially the same as that shown in FIGS. 8 and 15.

What is provided in the structure of FIG. 28 is a plurality of metering or constricting apertures or passageways as at 91 in lieu of the single constriction at 29 in FIG. 2. Accordingly, rotation of the control lever 102 will produce either an "off" or a meter condition relative to cylinder 101 and the passageways as at 91–94 within base housing 90. This will obtain for all stepped settings or the knob. The latter, however, may be rotated to a full-flow condition wherein full-flow aperture 96 will be brought in registry with wall aperture 95.

While particular embodiments of the invention have been shown and described, it will be obvious to those skilled in the art the various changes and modifications which may be made without departing from the essential features of the present invention and, therefore, the aim in the appended claims is to cover all such changes and modifications as fall within the true spirit and scope of the invention.

We claim:

1. A regulator device for vacuum systems including, in combination, a base housing having an air outlet, means mounted to and cooperable with said base housing for providing a variable, atmospheric air inlet to said base housing, said base housing having an air passageway means between said air outlet and said air inlet of a transverse open cross-sectional area not greater than .002 square inches.

2. The device of claim 1 wherein said transverse cross-sectional area is circular, having a diameter not lower than .050 inches.

3. The device of claim 1 wherein said air passageway means is disposed intermediate said air inlet and said air outlet.

4. The device of claim 1 wherein said base housing includes a hollow boss portion, said means including a control member provided with a cylinder portion, one of said hollow boss portion and said cylinder portion overlapping the remaining of said portions, said cylinder portion and hollow boss portion being provided with respective, registerable aperture means.

5. The device of claim 4 wherein said cylinder portion is exteriorly tapered, said hollow boss portion being interiorly tapered and receiving said cylinder portion.

6. The device of claim 4 wherein said hollow boss portion includes slot air passageways, said cylinder portion including a wall registration aperture selectively communicating with said slot air passageways.

7. The device of claim 6 wherein said cylinder portion and hollow boss portion are tapered, said slot passageways being closed-ended.

8. The device of claim 6 wherein said slot air passageways are mutually spaced and of progressively increasing depth, respectively.

9. The device of claim 6 wherein said slot air passageways are mutually spaced and of progressively increasing width, respectively 10. The device of claim 6 wherein said slot air passageways are arranged in groups of varying numbers of said slot air passageways.

11. The apparatus of claim 6 wherein said device includes a bezel member mounted to said base housing and revolvably receiving said control member, the juncture of said base housing and bezel being provided with peripherally disposed air-admittance aperture means.

12. The structure of claim 11 wherein said control member and bezel include mutually cooperable detent means and regulator vacuum-indicator means.

13. In combination, a body fluid aspiration bottle having a fluid inlet port and a vacuum port; adjustable, ambient air inlet regulator means for varying the negative pressure condition within said aspiration bottle; a vacuum, wall-fitting means; a vacuum source directly connected to said wall-fitting means, said regulator means being directly mounted to a selected one of said vacuum port and said wall-fitting means; and elongate conduit interconnecting said regulator means to the remaining one of said vacuum port and said wall-fitting means, said regulator means having ports constructed for such direct mounting.

14. A regulator device, for a negative pressure system, for adjustably leaking outside air into said system to control the negative pressure therein, said device including, in combination, a base housing means having a vacuum source coupling port and a system coupling port, said base housing means being provided with aperture means intercoupling said vacuum source coupling portion with said system coupling port, and a rotatable control member rotatably mounted to said base housing means and constructed for peripheral, ambient air flow into said base housing means and for discretely variably introducing outside air into said aperture means.

15. A regulator device, for a negative pressure system, for adjustably leaking outside air into said system to control the negative pressure therein, said device including, in combination, a base housing means having a vacuum source coupling port and a system coupling port, said base housing means provided with aperture means intercoupling said vacuum source coupling port with said system coupling port, and a rotatable control member rotatably mounted to said base housing means and constructed for variably introducing outside air into said aperture means and wherein said base housing means comprises a base housing member having an annular lip provided with an annular series of transverse airway slots and a bezel mounted over said annular lip, said control member being rotatably mounted to said bezel.

16. A regulator device, for a negative pressure system, for adjustably leaking outside air into said system to control the negative pressure therein, said device including, in combination, a base housing means having a vacuum source coupling port and a system coupling port, said base housing means being provided with aperture means intercoupling said vacuum source coupling port with said system coupling port, and a rotatable control member rotatably mounted to said base housing means and constructed for variably introducing outside air into said aperture means and wherein said aperture means has a transverse cross-section at one point not exceeding .002 square inches.

17. The device of claim 15 wherein said base housing includes an interior hollow boss portion provided with a series of slots of varying characteristics, and said control member including an interior hollow boss having a wall aperture overlapping selected ones of said slots, one of said hollow boss portion and said hollow boss overlapping the remaining ones.

18. A regulator device for vacuum systems, including, in combination, a base housing having an air outlet, means mounted to and cooperable with said base housing for providing a variable, atmospheric air inlet to said base housing, the combination of said providing means and said base housing providing at least on metering air-flow passageway communicating with said air outlet and having a transverse cross-section at at least one point defining a transverse open area not greater than .002 square inches.

19. The regulator device of claim 18 wherein said providing means comprises a rotatable, hollow, atmospheric-air communicative control member provided with a side wall aperture, said base housing having plural, mutually spaced, interior air passageways, with respective ones thereof comprising said air-flow passageway and being alignable with said side wall aperture upon rotation of said control member.

20. The regulator structure of claim 18 wherein said base housing includes an enlarged air passageway selectively registerable with said side wall aperture upon rotation of the latter.

21. The regulator device of claim 18 wherein said providing means comprises a rotatable control having a hollow interior and an extremity seating against said housing proximate said air outlet, said extremity including an arcuate slot in communication with said outlet throughout a rotational displacement of said control.

22. The regulator device of claim 18 wherein said base housing has an evacuating port proximate said bezel, said control being apertured such that the interior thereof is in air communication with said evacuating port.

23. The regulator device of claim 18 wherein said providing means comprises a control having an extension provided with an air passageway wall aperture, said base housing having a cylindrical portion provided with a series of air passageway means of progressively enlarged character and constructed for progressive registry of said side wall aperture upon rotation of said control.

24. The regulator device of claim 21 wherein said arcuate slot comprises a through-slot passing over a sector only of said air outlet.

25. The regulator device of claim 21 wherein said slot comprises a recess defining with said base housing proximate said air outlet a channel comprising said air-flow passage.

26. The regulator device of claim 24 wherein said arcuate slot terminates in an enlarged aperture registerable with said air outlet for essentially full vacuum condition at a region essentially interior of said control.

27. The regulator device of claim 25 wherein said arcuate slot terminates in an enlarged aperture registerable with said air outlet for essentially full vacuum condition at a region essentially interior of said control.

28. A regulator device for vacuum systems including, in combination, a base housing having an air outlet, adjustable means mounted to and cooperable with said base housing for providing a variable, atmospheric air inlet to said base housing, the combination of said base housing and said means being constructed to provide air-passageway constriction means for metering air passage to and through said air outlet, said constriction means defining at least one metering, air-travel passageway having not greater than a 0.002 square inch cross section.

29. The regulator of claim 28 wherein said base housing also includes a full-vacuum enlarged air passageway essentially parallel to said constriction means and larger than the cross-section area thereof.

30. Structure according to claim 28 wherein said base housing has an interior air-passageway blocking region to selectively block base-housing air communications therethrough.

* * * * *